(12) United States Patent
Kriksunov et al.

(10) Patent No.: US 8,313,768 B2
(45) Date of Patent: Nov. 20, 2012

(54) MANUFACTURE OF TABLET HAVING IMMEDIATE RELEASE REGION AND SUSTAINED RELEASE REGION

(75) Inventors: Leo B. Kriksunov, Ithaca, NY (US); Harry S. Sowden, Glenside, PA (US); Joseph R. Luber, Quakertown, PA (US); Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 12/887,560

(22) Filed: Sep. 22, 2010

(65) Prior Publication Data

US 2011/0070304 A1    Mar. 24, 2011

Related U.S. Application Data

(60) Provisional application No. 61/245,315, filed on Sep. 24, 2009, provisional application No. 61/255,582, filed on Oct. 28, 2009, provisional application No. 61/314,629, filed on Mar. 17, 2010, provisional application No. 61/358,167, filed on Jun. 24, 2010.

(51) Int. Cl.
*A61K 9/22* (2006.01)
*A61P 29/00* (2006.01)
*B29C 35/02* (2006.01)
*B29C 43/02* (2006.01)
*B29C 35/08* (2006.01)

(52) U.S. Cl. ........ 424/468; 424/464; 424/465; 424/475; 264/239; 264/462

(58) Field of Classification Search .................. 424/468, 424/464, 465, 475; 264/239, 462
See application file for complete search history.

(56) References Cited

U.S. PATENT DOCUMENTS

| | | |
|---|---|---|
| 2,183,053 A | 12/1939 | Taylor |
| 2,887,437 A | 5/1959 | Klioze et al. |
| 3,670,065 A | 6/1972 | Eriksson et al. |
| 3,885,026 A | 5/1975 | Heinemann et al. |
| 4,158,411 A | 6/1979 | Hall et al. |
| 4,173,626 A | 11/1979 | Dempski et al. |
| 4,260,596 A | 4/1981 | Mackles |
| 4,268,238 A | 5/1981 | Marc |
| 4,268,465 A | 5/1981 | Suh et al. |
| 4,327,076 A | 4/1982 | Puglia et al. |
| 4,398,634 A | 8/1983 | McClosky |
| 4,590,075 A | 5/1986 | Wei et al. |
| 4,609,543 A | 9/1986 | Morris et al. |
| 4,642,903 A | 2/1987 | Davies |
| 4,684,534 A | 8/1987 | Valentine |
| 4,758,439 A | 7/1988 | Godfrey |
| 4,762,719 A | 8/1988 | Forester |
| 4,824,681 A | 4/1989 | Schobel et al. |
| 4,828,845 A | 5/1989 | Zamudio-Tena et al. |
| 4,832,956 A | 5/1989 | Gergely et al. |
| 4,851,226 A | 7/1989 | Julian et al. |
| 4,857,331 A | 8/1989 | Shaw et al. |
| 4,863,742 A | 9/1989 | Panoz et al. |
| 4,906,478 A | 3/1990 | Valentine et al. |
| 4,979,720 A | 12/1990 | Robinson |
| 4,980,170 A | 12/1990 | Schneider et al. |
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,112,616 A | 5/1992 | McCarty |
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Webling et al. |
| 5,215,755 A | 6/1993 | Roche et al. |
| 5,223,264 A | 6/1993 | Webling et al. |
| 5,262,171 A | 11/1993 | Login et al. |
| 5,275,822 A | 1/1994 | Valentine et al. |

(Continued)

FOREIGN PATENT DOCUMENTS

EP    0 070 127    1/1983

(Continued)

OTHER PUBLICATIONS

Int'l Search Report for Application No. PCT/US2008/081496, dated Jul. 15, 2009.
Int'l Search Report for Application No. PCT/US2008/74375, dated Nov. 17, 2008.
Int'l Search Report for Application No. PCT/US2010/049909 dated Dec. 3, 2010.
Int'l Search Report for Application No. PCT/US2010/049925 dated Dec. 8, 2010.
Int'l Search Report for Application No. PCT/US2010/049931 dated Jan. 7, 2011.
Int'l Search Report for Application No. PCT/US2010/049933 dated Feb. 15, 2011.

(Continued)

*Primary Examiner* — Anoop Singh
*Assistant Examiner* — Anna Falkowitz
(74) *Attorney, Agent, or Firm* — William E. McGowan

(57) ABSTRACT

In one aspect, the present invention features a process for making a tablet including a pharmaceutically active agent wherein the tablet has both an immediate release region and a modified release region. The method includes the steps of: (a) forming a tablet shape including a powder blend containing a pharmaceutically active agent and a thermally-sensitive material; and (b) applying energy in different amounts to different regions of the tablet shape to form the tablet in a manner such that: (i) a first region of the tablet shape is exposed to said energy for a sufficient period of time to melt the thermally-sensitive material within the first region to form said modified release region of said tablet; and (ii) a second region of said tablet shape is not so exposed to the energy such that said second region forms the immediate release region of said tablet.

15 Claims, 2 Drawing Sheets

U.S. PATENT DOCUMENTS

| | | | |
|---|---|---|---|
| 5,286,497 A | 2/1994 | Hendrickson et al. | |
| 5,320,848 A | 6/1994 | Geyer et al. | |
| 5,330,763 A | 7/1994 | Gole et al. | |
| 5,464,632 A | 11/1995 | Cousin et al. | |
| 5,489,436 A | 2/1996 | Hoy et al. | |
| 5,501,858 A | 3/1996 | Fuisz | |
| 5,501,861 A | 3/1996 | Makino et al. | |
| 5,503,846 A | 4/1996 | Wehling et al. | |
| 5,558,880 A | 9/1996 | Gole et al. | |
| 5,560,963 A | 10/1996 | Tisack | |
| 5,587,172 A | 12/1996 | Cherukuri et al. | |
| 5,587,179 A | 12/1996 | Gergely et al. | |
| 5,607,697 A | 3/1997 | Alkire et al. | |
| 5,622,719 A | 4/1997 | Myers et al. | |
| 5,631,023 A | 5/1997 | Kearney et al. | |
| 5,635,210 A | 6/1997 | Allen, Jr. et al. | |
| 5,648,093 A | 7/1997 | Gole et al. | |
| 5,653,993 A | 8/1997 | Ghanta et al. | |
| 5,662,849 A | 9/1997 | Bogne et al. | |
| 5,720,974 A | 2/1998 | Makino et al. | |
| 5,886,081 A | 3/1999 | Sternowski | |
| 5,912,013 A | 6/1999 | Rudnic et al. | |
| 5,997,905 A | 12/1999 | McTeigue et al. | |
| 6,024,981 A | 2/2000 | Khankari et al. | |
| 6,060,078 A | 5/2000 | Lee | |
| 6,103,260 A | 8/2000 | Luber et al. | |
| 6,224,905 B1 | 5/2001 | Lawrence et al. | |
| 6,228,398 B1 | 5/2001 | Devane et al. | |
| 6,258,381 B1 * | 7/2001 | Luber et al. | 424/464 |
| 6,270,805 B1 | 8/2001 | Chen et al. | |
| 6,277,409 B1 | 8/2001 | Luber et al. | |
| 6,284,270 B1 | 9/2001 | Lagoviyer et al. | |
| 6,316,026 B1 | 11/2001 | Tatara et al. | |
| 6,322,819 B1 | 11/2001 | Burnside et al. | |
| 6,328,994 B1 | 12/2001 | Shimizu et al. | |
| 6,465,010 B1 | 10/2002 | Lagoviyer et al. | |
| 6,499,984 B1 | 12/2002 | Ghebre-Sellassie et al. | |
| 6,569,463 B2 | 5/2003 | Patel et al. | |
| 6,589,554 B1 | 7/2003 | Mizumoto et al. | |
| 6,649,888 B2 | 11/2003 | Ryan et al. | |
| 6,753,009 B2 | 6/2004 | Luber et al. | |
| 6,767,200 B2 | 7/2004 | Sowden et al. | |
| 6,814,978 B2 | 11/2004 | Bunick et al. | |
| 6,932,979 B2 | 8/2005 | Gergely | |
| 7,157,100 B2 | 1/2007 | Doshi et al. | |
| 2001/0033831 A1 | 10/2001 | Chow et al. | |
| 2002/0012701 A1 * | 1/2002 | Kolter et al. | 424/468 |
| 2002/0018800 A1 | 2/2002 | Pinney et al. | |
| 2002/0079121 A1 | 6/2002 | Ryan et al. | |
| 2002/0122822 A1 | 9/2002 | Bunick et al. | |
| 2003/0021842 A1 | 1/2003 | Lagoviyer et al. | |
| 2003/0068373 A1 | 4/2003 | Luber et al. | |
| 2003/0161879 A1 | 8/2003 | Ohmori et al. | |
| 2003/0194442 A1 | 10/2003 | Guivarch et al. | |
| 2003/0224044 A1 | 12/2003 | Weibel | |
| 2004/0137057 A1 | 7/2004 | Sowden et al. | |
| 2004/0156902 A1 | 8/2004 | Lee et al. | |
| 2004/0191499 A1 | 9/2004 | Hallett et al. | |
| 2005/0019407 A1 * | 1/2005 | Sowden et al. | 424/472 |
| 2006/0034927 A1 | 2/2006 | Casadevall et al. | |
| 2006/0134195 A1 | 6/2006 | Fu et al. | |
| 2007/0196477 A1 | 8/2007 | Witham et al. | |
| 2007/0281009 A1 | 12/2007 | Kamisono et al. | |
| 2008/0286340 A1 | 11/2008 | Andersson et al. | |
| 2009/0060983 A1 | 3/2009 | Bunick et al. | |
| 2009/0110716 A1 | 4/2009 | Bunick et al. | |

FOREIGN PATENT DOCUMENTS

| | | | |
|---|---|---|---|
| EP | 0192460 B1 | | 8/1986 |
| EP | 0 416 791 A2 | | 3/1991 |
| GB | 772 315 | | 4/1957 |
| GB | 1 097 207 | | 12/1967 |
| JP | 59 067006 A | | 4/1984 |
| WO | WO 91/12881 | | 9/1991 |
| WO | WO 92/06679 | | 4/1992 |
| WO | WO 93/13758 A1 | | 7/1993 |
| WO | WO 94/06416 | * | 3/1994 |
| WO | WO 95/09044 A1 | | 4/1995 |
| WO | WO 97/38679 A2 | | 10/1997 |
| WO | WO 98/32426 A1 | | 7/1998 |
| WO | WO 99/17771 | | 4/1999 |
| WO | WO 99/44580 A1 | | 9/1999 |
| WO | WO 00/04281 | | 1/2000 |
| WO | WO 03/101431 A1 | | 12/2003 |
| WO | WO 2004/000197 A2 | | 12/2003 |
| WO | WO 2004/046296 A1 | | 6/2004 |
| WO | WO 2006/127618 | | 11/2006 |
| WO | WO 2007/042153 A1 | | 4/2007 |
| WO | WO 2008/005318 A2 | | 1/2008 |
| WO | WO 2008/015221 A2 | | 2/2008 |
| WO | WO 2010/058218 A1 | | 5/2010 |

OTHER PUBLICATIONS

Int'l Search Report for Application No. PCT/US2010/049964 dated Dec. 30, 2010.

Int'l Search Report for Application No. PCT/US2010/049971 dated Jan. 7, 2011.

U.S. Appl. No. 11/847,444, filed Aug. 30, 2007—Pending.
U.S. Appl. No. 12/570,046, filed Sep. 30, 2009—Pending.
U.S. Appl. No. 12/260,151, filed Oct. 29, 2008—Pending.
U.S. Appl. No. 12/566,078, filed Sep. 24, 2009—Pending.
U.S. Appl. No. 12/566,096, filed Sep. 24, 2009—Pending.
U.S. Appl. No. 12/887,544, filed Sep. 22, 2010—Pending.
U.S. Appl. No. 12/887,552, filed Sep. 22, 2010—Pending.
U.S. Appl. No. 12/887,560, filed Sep. 22, 2010—Pending.
U.S. Appl. No. 12/887,564, filed Sep. 22, 2010—Pending.
U.S. Appl. No. 12/887,569, filed Sep. 22, 2010—Pending.
U.S. Appl. No. 12/887,575, filed Sep. 22, 2010—Pending.
U.S. Appl. No. 12/887,582, filed Sep. 22, 2010—Pending.
U.S. Appl. No. 12/887,593, filed Sep. 22, 2010—Pending.

Jones, P. L. et al, "Dielectric Drying", Drying Technology, 14(5), 1996, p. 1063-1098.

Guo, et al., Temperature and Moisture Dependent Dielectric Properties of Legume Flour Associated with Dielectric Heating, LWT Food Science and Technology 43, 2010, p. 193-201.

Katsuki, et al., Novel Energy-Saving Materials for Microwave Heating, Chem Mater. 2008, 20, p. 4803-4807.

Radio-Frequency Heating of Plastics, TechCommentary, vol. 4, No. 2, 1987, p. 1-4.

Jones, P. L., High Frequency Dielectric Heating in Paper Making, Drying Technology, 4(2), 1986, p. 217-244.

What is R.F. Heat Sealing?, Dielectric Sealing Service, Inc., 2007, p. 1-6.

Broadband RF Survey Instruments, ETS•Lindgren Haladay EMF Measurement, 2002, p. 1-2.

Lamp IR Infrared Heaters: Infrared Lamps for Controlled Concentrated Heating, Research Inc., p. 1-20., Sep. 20, 2010.

Callebaut, Power Quality & Utilisation Guide, Section 7: Energy Efficiency, Mar. 2007, www.leonardo-energy.org, p. 1-9.

Shukla, et al., Mouth Dissolving Tablets I: An Overview of Formulation Technology, Sci Pharm 2009, 76: p. 309-326.

Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.

Lachman, Leon et al., "The Theory and Practice of Industrial Pharmacy", $3^{rd}$ Ed., Chapter 11, pp. 293-345,Lea & Febiger, 1986, Philadelphia.

McConville, J. et al., "Erosion characteristics of an erodible tablet incorporated in a time-delayed capsule device," Drug Development and Industrial Pharmacy, vol. 31, No. 1, 2005, pp. 79-89, XP008108019.

USP 23 (1995) 1216, Tablet Friability, p. 1981.

USP 24, 2000 Version, Acetaminophen, pp. 19-20 and Ibuprofen, p. 856 (1999).

USP 30-NF25, Disintegration, pp. 276-277.

USP 33—U.S. Pharmacopeia, General Chapter 701—Disintegration, 2008.

Orally Disintegrating Tablets, draft Food and Drug Administration Guidance, Apr. 2007.

Heng, Paul Wan Sia, Chem Pharm Bull, 47 (5) 633-638 (1999).

Koral, Tony, Radio Frequency Heating and Post-Baking, Biscuit World, Issue 4, vol. 7, Nov. 2004.
Dielectric Heating with Microwave Energy, Püschner MikrowellenEnergietechnik, pp. 1-4.
Amin, Avani F., Emerging Treands in the Development of Orally Disintegrating Tablet Technology, Pharmainfo.net, vol. 4, Issue 1, Jan. 26, 2006; pp. 1-30.
Matthes, R.; "Chapter 49" from website: htt.://www.ilo.org/safework_bookshelf/english?content&nd=857170571; made available online Oct. 12, 2004.
Google page showing the availability date of web reference U; provided Mar. 15, 2011.
Dielectric Heating with Microwave Energy, Püschner MikrowellenEnergietechnik, pp. 1-4, Jun. 1997.
USP 30-NF25, Disintegration, pp. 276-277, 2007.
U.S. Appl. No. 13/052,316, filed Mar. 21, 2011—Pending.
U.S. Appl. No. 13/052,219, filed Mar. 21, 2011—Pending.
U.S. Appl. No. 13/052,200, filed Mar. 21, 2011—Pending.
U.S. Appl. No. 13/246,884, filed Sep. 28, 2011—Pending.
Rambali, B., et al., International Journal of Pharmaceutics 220 (2001), pp. 129-140.
Radio Frequency Company, Microwave, (Feb. 19, 2004), pp. 1-2.

* cited by examiner

MANUFACTURE OF TABLET HAVING IMMEDIATE RELEASE REGION AND SUSTAINED RELEASE REGION

CROSS REFERENCE TO RELATED APPLICATIONS

This application claims priority of the benefits of the filing of U.S. Provisional Application Ser. No. 61/245,315, filed Sep. 24, 2009, U.S. Provisional Application Ser. No. 61/255,582, filed Oct. 28, 2009, U.S. Provisional Application Ser. No. 61/314,629, filed Mar. 17, 2010, and U.S. Provisional Application Ser. No. 61/358,167, filed Jun. 24, 2010. The complete disclosures of the aforementioned related U.S. patent applications are hereby incorporated herein by reference for all purposes.

BACKGROUND OF THE INVENTION

Modified release pharmaceutical dosage forms have long been used to optimize drug delivery and enhance patient compliance, especially by reducing the number of doses of medicine the patient must take in a day. Well known mechanisms by which a dosage form (or drug delivery system) can deliver drug at a modified rate (e.g. sustained or delayed release) include diffusion, erosion, and osmosis. An important objective of modified release dosage forms is to provide a desired blood concentration versus time profile for the drug. Fundamentally, the pharmacokinetic profile for a drug is governed by the rate of absorption of the drug into the blood, and the rate of elimination of the drug from the blood. To be absorbed into the blood (circulatory system), the drug must first be dissolved in the gastrointestinal fluids. For those relatively rapidly absorbed drugs whose dissolution in gastrointestinal fluids is the rate limiting step in drug absorption, controlling the rate of dissolution (i.e. drug release from the dosage form) allows the formulator to control the rate of drug absorption into the circulatory system of a patient. The type of PK profile, and correspondingly, the type of dissolution or release profile desired, depends on, among other factors, the particular pharmaceutically active agent and physiological condition being treated.

U.S. Pat. No. 6,228,398 discloses solid dosage forms which contain a multiparticulate system of modified release and immediate release pharmaceutically active agents such that the pharmaceutically active agent is supplied in a pulsatile manner. However, multiparticulate systems disadvantageously have the added cost and processing associated with adding modified release layers to particulates which contain the pharmaceutically active agents.

U.S. Pat. No. 7,157,100 discloses solid dosage forms which contain multiple layers wherein one or more layers contains pharmaceutically active agent to be delivered in an immediate release manner and one or more layers contains pharmaceutically active agent to be displayed in a modified release manner. The dosage form delivers the pharmaceutically active agent such that the composition can be supplied in a once per day dosing regimen. However, multiple layers of a dosage form must be prepared in multiple stations and with multiple blends, adding complexity to the preparation of the dosage form.

Thus, there is a need to develop a process for making a tablet wherein both an immediate release region and the modified release region can be made from the same powder blend.

SUMMARY OF THE INVENTION

In one aspect, the present invention features a process for making a tablet including a pharmaceutically active agent wherein the tablet has both an immediate release region and a modified release region. The method includes the steps of: (a) forming a tablet shape including a powder blend containing a pharmaceutically active agent and a thermally-sensitive material; and (b) applying energy in different amounts to different regions of the tablet shape to form the tablet in a manner such that: (i) a first region of the tablet shape is exposed to said energy for a sufficient period of time to melt the thermally-sensitive material within the first region to form said modified release region of said tablet; and (ii) a second region of said tablet shape is not so exposed to the energy such that said second region forms the immediate release region of said tablet.

In one aspect, the present invention features tablet including both an immediate release region and a modified release region wherein both the immediate release region and the modified release region comprise the same pharmaceutically active agent and the same thermally-sensitive material; provided, however, the modified release region has been sintered with said thermally-sensitive material while the immediate release region has not been sintered with said thermally-sensitive material.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features a novel process for manufacturing a tablet having both an immediate release region and a modified release region that utilize the same powder blend. The process, thus, allows for the minimization of powder blends needed to produce the tablet. In one embodiment, as the two regions can be manufactured from the same powder blend as opposed to having to two separate powder blends (as in conventional bi-layer tablets), the process allows for high tableting and compression production rates and allows for a lower development time since only one powder blend is required to be developed for both regions.

The softening, melting, or cross-linking of the thermally-sensitive material(s) in the application of energy in the process of the present invention results in the sintering of the tablet shape in certain regions of the tablet shape through the binding of the softened, melted, or cross-linked thermally-sensitive material with the pharmaceutically active agent and/or other ingredients within the compacted powder blend. The sintering of such regions results in the formation of a modified release region of the tablet (first region).

Figure 2:
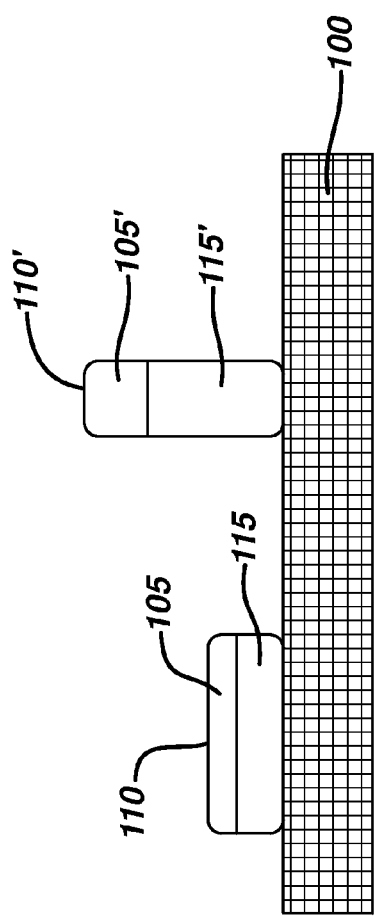
FIG. 2 is a side view of tablet shape 110/110' being heated by energy source 100.

In one embodiment, as shown in FIG. 2, the tablet 110 has two regions, first region 115 which has been heated by heat source 100 such that it is a modified release region and second region 105 which remains an immediate release region. In this embodiment, there is a transition of solubility within the first region 115 in the extent and level to which the thermally-sensitive material has been softened or melted. Specifically, the portion of the first region 115 that is closer to the heat source 100 has received more energy while the portion of the first region 115 that is further away from the heat source (e.g., closer to the second region 105) has received less energy. In this embodiment, the portion of the first region 115 that is closer to the heat source 100 will exhibit less dissolution, and consequently a more pronounced modified-release profile, than the portion of the first region 115 that is further away from the heat source.

In one embodiment, in the first region, the thermally-sensitive material may stay as a discreet, dispersed powder, and/or may completely melt, and in which case the thermally-sensitive material may migrate between particles comprising the active ingredient and other un-melted particles of the blend, causing those materials to tack together upon cooling and re-solidification of the thermally-sensitive material which can inhibit water from entering that region of the tablet and modify the release of the pharmaceutically active ingredient from such region.

In one embodiment, there is a transition in the first region. For example, in looking at FIG. 2, the portion of the first region 115 that is closer to heat source 100 (and consequently received more heat) has more of the thermally-sensitive material melted and, consequently, has a longer period of modified release of the pharmaceutically active ingredient. Conversely, the portion of the first region 115 that is further from the heat source 100 and closer to the second region (and consequently received less heat) has less of the thermally-sensitive material melted and, consequently, has a shorter period of modified release of the pharmaceutically active ingredient.

In one embodiment, the first region comprises at least 20%, by weight, of said tablet, such as at least 50%, by weight, of said tablet. In one embodiment, the second region comprises at least 20%, by weight, of said tablet, such as at least 50%, by weight, of said tablet, such as at least 80%, by weight, of said tablet.

In one embodiment, the first region is less soluble in water than the second region. In one embodiment, the thermally-sensitive material is soluble at a value less than 0.01 g/L in water at 25° C. In another embodiment, the first region slightly soluble in aqueous media, with a solubility less than about 500 g/L in water at 25° C., such as less than about 10 g/L, such as less than about 1 g/L.

In one embodiment, the tablet has a therapeutic effect of at least 8 hours, such as at least 12 hours, such as at least 24 hours.

What is meant by an "immediate release region" is a region of the tablet where the majority (e.g., substantially all or all) of the pharmaceutically active agent within such region is released within a relatively short time, for example within 1 hour, preferably within 30 minutes, after oral ingestion. What is meant by a "modified release region" is that the region is not an immediate release region, e.g., the release of the pharmaceutically active agent is controlled, sustained, extended, retarded, prolonged, delayed and the like.

In one embodiment, the dissolution characteristics of the pharmaceutically active agent within the immediate release region of the tablet meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999).

In one embodiment the pharmaceutically active agent in the tablet is released in the following manner, from about 1 to 50 percent is released in the 60 minutes following oral ingestion and about 50 to 99 percent is released from about 60 minutes to about 24 hours after oral ingestion, such as from about 20 to 50 percent is released in the 60 minutes following oral ingestion and about 50 to 80 percent is released from about 60 minutes to about 24 hours after oral ingestion.

In one embodiment the controlled release portion is defined a portion containing at least one active ingredient that is released into the bloodstream in a substantially continuous manner over a controlled period of time such as, for example, about 4 hours, such as about 8 hours, such as about 12 hours, such as about 12 hours after initial oral ingestion of the tablet.

Powder Blend

As discussed above, the tablet is manufactured by compacting a powder blend containing a pharmaceutically active agent (as discussed herein), thermally-sensitive material, and optionally a pharmaceutically-acceptable carrier. The carrier contains one or more suitable excipients for the formulation of tablets. Examples of suitable excipients include, but are not limited to, fillers, adsorbents, disintegrants, lubricants, glidants, sweeteners, superdisintegrants, flavor and aroma agents, antioxidants, preservatives, texture enhancers, and mixtures thereof. One or more of the above ingredients may be present on the same particle of the powder blend.

Suitable fillers include, but are not limited to, carbohydrates (as discussed herein) and water insoluble plastically deforming materials (e.g., microcrystalline cellulose or other cellulosic derivatives), and mixtures thereof.

Suitable adsorbents include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.)), clays, silicas, bentonite, zeolites, magnesium silicates, hydrotalcite, veegum, and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners include, but are not limited to, synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside; sugar alcohols such as sorbitol, mannitol, glycerol, lactitol, malitol, and xylitol; sugars extracted from sugar cane and sugar beet (sucrose), dextrose (also called glucose), fructose (also called laevulose), and lactose (also called milk sugar); isomalt, salts thereof, and mixtures thereof.

Examples of superdisintegrants include, but are not limited to, croscarmellose sodium, sodium starch glycolate and cross-linked povidone (crospovidone). In one embodiment the tablet contains up to about 5% by weight of such superdisintegrant.

Examples of suitable flavor and aroma agents include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry, and black currant); artificial and natural flavors of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus *Nicotiana* in amounts not contributing significantly to a level of therapeutic nicotine), and mixtures thereof.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment of the invention, the powder blend has an average particle size of less than 500 microns, such as from about 50 microns to about 500 microns, such as from about 50 microns and 300 microns. Particles in this size range are particularly useful for direct compacting processes.

In one embodiment of the invention, the tablet may be a made from a powder blend that is substantially free of hydrated polymers. As used herein, what is meant by "substantially free" is less than 5%, such as less than 1%, such as less than 0.1%, such as completely free (e.g., 0%). Examples of hydrated polymers include high molecular weight hydroxyalkylcelluloses. By "high weight average molecular weight hydroxyalkylcellulose," it is meant a hydroxyalkylcellulose having a) weight average molecular weight between about 60,000 to about 5,000,000, e.g. from about 140,000 to about 1,150,000; and/or b) a viscosity between about 3,000 mPa·s to about 150,000 mPa·s in a 2% aqueous solution, e.g., from about 4,000 mPa·s to about 100,000 mPa·s in a 2% aqueous solution. "Hydroxyalkylcellulose," as used herein shall mean cellulose derivatives that are substituted with a hydroxyalkyl group, wherein the alkyl group contains from about 1 to about 10 carbons. Examples of suitable high molecular weight hydroxyalkylcelluloses include, but are not limited to, hydroxymethylcellulose, hydroxyethylcellulose, hydroxypropylcellulose, hydroxyethylmethylcellulose, hydroxypropylmethylcellulose, and the like. In one embodiment, the hydroxyalkylcellulose is hydroxypropylcellulose and/or hydroxypropylmethylcellulose. Examples of suitable hydroxypropylmethylcelluloses include those available from Dow Chemical Corporation under the tradenames, "HPMC K4M," "HPMC K15M," and "HPMC K100M." Examples of suitable hydroxypropylcelluloses include those available from Hercules, Inc. under the tradenames, "Klucel H(CS) and "Klucel M".

In one embodiment the dosage form of the present invention is substantially free of insoluble film forming polymers. Examples of insoluble film forming polymers include cellulose acetate, cellulose acetate butyrate, cellulose triacetate, ethylcellulose, neutral ester co-polymer of ethyl acrylate and methyl methacrylate, which is commercially available from Rohm Pharma under the tradename, "EUDRAGIT NE", and poly(ethyl acrylate, methyl methacrylate, trimethylammonioethyl methacrylate chloride) 1:2:0.1, which is commercially available from Rohm Pharma under the tradename, "EUDRAGIT RS". One or more than one insoluble film forming polymer may be used. Preferably, the insoluble film forming polymer is impermeable and does not swell in an aqueous environment. More preferably, the insoluble film forming polymer is selected from cellulose acetate and ethylcellulose.

This composition of the present invention is advantageous for maintaining an immediate release dissolution profile, minimizing processing and material costs, and providing for optimal physical and chemical stability of the tablet. In one embodiment, the density of the tablet is greater than about 0.9 g/cc.

In one embodiment, powder blend/ tablet is substantially free of a directly compressible water insoluble fillers. Water insoluble fillers include but are not limited to microcrystalline cellulose, directly compressible microcrystalline cellulose, celluloses, water insoluble celluloses, starch, cornstarch and modified starches. As described in this embodiment substantially free is less than 2 percent, e.g. less than 1 percent or none.

In one embodiment, there is a single powder blend forming the tablet shape which is then heated with the energy. In another embodiment, the tablet is formed of at least two different powder blends, at least one powder blend being curable by the addition of energy and at least one formulation not being so curable. When cured with energy (e.g., RF energy), such tablet shape develops two or more dissimilarly cured zones. In one embodiment, the outside area of the tablet shape is cured, while the middle of the tablet shape is not cured. By adjusting the focus of the heating (e.g., the shape of the RF electrodes), the heat delivered to the tablet shape can be focused to create customized softer or harder areas on the finished tablet.

Thermally-Sensitive Material

In one embodiment, the powder blend/tablet of the present invention includes at least one thermally-sensitive material. In one embodiment, the thermally-sensitive material is a meltable material having a melting point of from about 20° C. to about 140° C., such as from about 55 to about 100° C. The softening, melting, or cross-linking of the thermally-sensitive material(s) results in the sintering of the tablet shape in certain regions of the tablet shape through the binding of the softened or melted material with the pharmaceutically active agent and/or other ingredients within the compacted powder blend. The sintering of such regions results in the formation of a modified release region of the tablet.

In one embodiment, the thermally-sensitive material is sensitive to conduction, convection, and/or infrared energy. Examples of such thermally-sensitive materials include, but are not limited to, cetyl alcohol, fatty acid esters such as sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides; phospholipids such as phospholipids include phosphotidyl choline, phosphotidyl serene, phosphotidyl enositol, and phosphotidic acid; waxes such as carnauba wax, spermaceti wax, beeswax, candelilla wax, shellac wax, microcrystalline wax, and paraffin wax; and fats such as hydrogenated vegetable oils such as for example cocoa butter, hydrogenated palm kernel oil, hydrogenated cottonseed oil, hydrogenated sunflower oil, and hydrogenated soybean oil; and free fatty acids and their salts; polymers such as polyvinylacetate and polycaprolactone; and mixtures thereof.

In one embodiment, the thermally-sensitive material is a RF-thermally-sensitive material. What is meant by an RF-thermally-sensitive material is a solid material that can be softened or melted upon exposure to RF energy. The RF-thermally-sensitive material typically is polar and has the capability to re-harden or resolidify upon heating. Examples of such materials include, but are not limited to, polyethylene glycol and polyethylene oxide.

In one embodiment the thermally-sensitive material is insoluble in aqueous media, e.g. the thermally-sensitive material is soluble at a value less than 0.01 g/L in water at 25° C. In another embodiment, the thermally-sensitive material is slightly soluble in aqueous media, with a solubility less than about 500 g/L in water at 25° C., such as less than about 10 g/L, such as less than about 1 g/L.

In one embodiment the thermally-sensitive material has a quantifiable hydrophile-lipofile balance or "HLB" value. The lower HLB values represent lower water solubility and higher HLB values represent higher water solubility. In one embodiment the thermally-sensitive material has an HLB value of between 1 and 6 representing lower solubility, and in another embodiment the thermally-sensitive material has an HLB value between 7-13, representing higher solubility.

The thermally-sensitive material(s) may be present at level of about 2 percent to about 95 percent of the powder blend/tablet, such as from about 5 percent to about 75 percent, such as from about 5 percent to about 50 percent, such as from about 5 percent to about 30 percent of the powder blend/tablet.

Pharmaceutically Active Agent

The powder blend/tablet of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and anti-flatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the tablet is selected from phenylephrine, dextromethorphan, pseudoephedrine, acetaminophen, cetirizine, aspirin, nicotine, ranitidine, ibuprofen, ketoprofen, loperamide, famotidine, calcium carbonate, simethicone, chlorpheniramine, methocarbomal, chlophedianol, ascorbic acid, pectin, dyclonine, benzocaine and menthol, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for compaction or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles, which are encapsulated with ethylcellulose or other polymers by a coacervation process, may be used in the present invention. Coaccervation-encapsulated acetaminophen may be purchased commercially from Eurand America, Inc. (Vandalia, Ohio) or from Circa Inc. (Dayton, Ohio).

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, sustained release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

Examples of swellable, erodible hydrophilic materials for use as a release modifying excipient for use in the modified release coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of suitable thermoplastic polyalkylene oxides include poly (ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as release-modifying excipients for use in the modified release coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent. In one embodiment, the coating which is used in the coated particle of the pharmaceutically active agent is substantially free of a material (such as polyethylene glycol) which melts below 85° C., in order to prevent damage to the integrity of the coating during the heating step.

In one embodiment one or more pharmaceutically active agents or a portion of the pharmaceutically active agent may be bound to an ion exchange resin for the purposes of taste-masking the pharmaceutically active agent or delivering the active in a modified release manner The melting point of the pharmaceutically active agent can have an impact on the temperature used during the heating step and the type of the thermally-sensitive material used. In one embodiment, the melting point of the thermally-sensitive material is less than the melting point of the pharmaceutically active agent. In another embodiment, the melting point of the pharmaceutically active agent is the same or lower than the melting point of the thermally-sensitive material. In one embodiment, the heating temperature is above the melting dehydration temperature of the thermally-sensitive material and below the melting point of the pharmaceutically active agent. In one embodiment wherein ibuprofen is the pharmaceutically active agent, the thermally-sensitive material is heated from about 30° C. to about 60° C.

In one embodiment, the processing of the tablet is free of a wet or hot melt granulation step. In this embodiment, the materials are directly blended prior to the addition of heat. In one embodiment, the materials are directly blended and compacted prior to the addition of heat.

Manufacture of Tablet Shape

Figure 1:
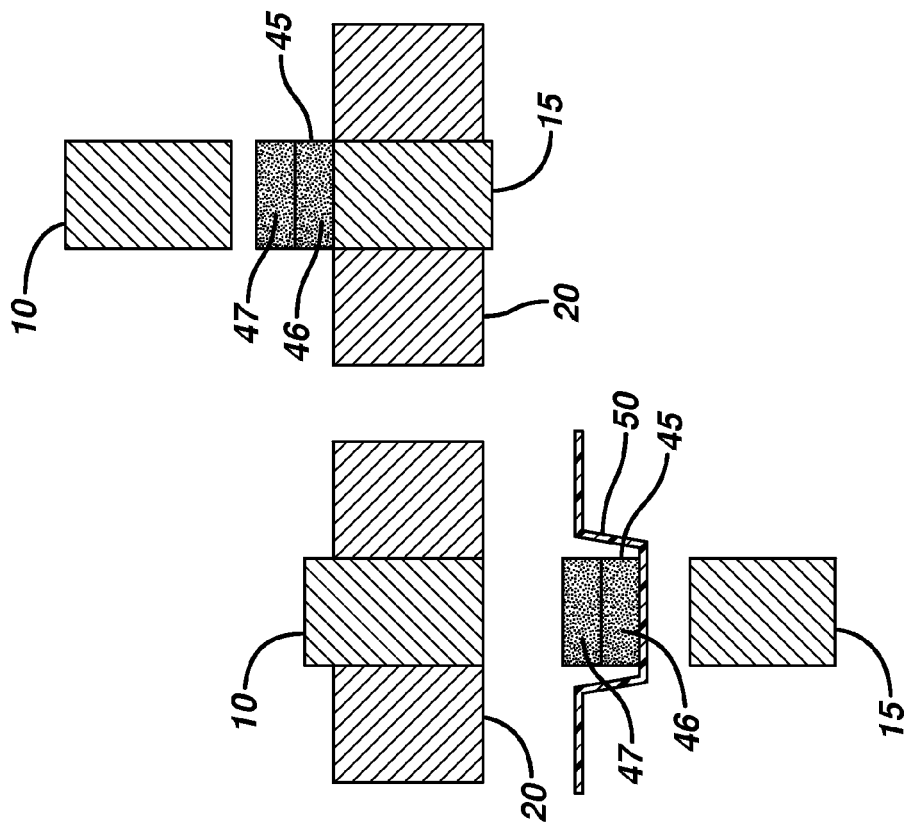
FIG. 1A is a side view of an embodiment of the invention showing powder blend 30 filled into the forming cavity of die platen 20.
FIG. 1B is a side view of an embodiment of the invention showing tablet shape 40 between an upper forming tool 10 and a lower forming tool 15.
FIG. 1C is a side view of an embodiment of the invention showing tablet 45 pushed by the upper forming tool 10 from die platen 20 into blister 50.
FIG. 1D is a side view of an embodiment of the invention showing tablet 45 pushed from the die platen 20 by the lower forming tool 15.

The tablet shape may be made by various methods known in the art, such as compaction, extrusion, or injection molding. In one embodiment, the tablet shape is made by a compaction (e.g., compression using a tablet press). In one embodiment where a tablet press in used, the powder blend is fed into the cavity of a die platen of an apparatus that applies pressure to form a tablet shape. Any suitable compacting apparatus may be used, including, but not limited to, a conventional unitary or rotary tablet press. In one embodiment, the tablet shape may be formed by compaction using a rotary tablet press (e.g., such as those commercially available from Fette America Inc., Rockaway, N.J. or Manesty Machines LTD, Liverpool, UK). In one embodiment, where the tablet shape is manufactured in a tablet press, the tablet is heated after it is removed from the tablet press. In another embodiment, the tablet is heated within the tablet press. In such an embodiment, as shown in FIG. 1A, a metered volume of powder blend 30 is filled into the forming cavity of die platen 20, where the powder blend 30 is either gravity fed or mechanically fed from a feeder (not shown) of the rotary tablet press, and the die platen rotates as part of a "die table" from the filling position (FIG. 1A) to a compaction position (FIG. 1B). At the compaction position (FIG. 1B), the powder blend 30 is compacted between an upper forming tool 10 (e.g., a die punch) and a lower forming tool 15 to form a tablet shape 40. The resulting tablet shape 40 is then exposed to energy (e.g., thermal energy from punch 10) to form the tablet 45 having a first region 47 and a second region 46. In one embodiment as shown in FIG. 1C, the tablet 45 is pushed by the upper forming tool 10 from die platen 20 into a blister 50 used to package the tablet 45. In an alternative embodiment shown in FIG. 1D, the tablet 45 is pushed from pie platen 20 by the lower forming tool 15 and guided to an injection chute by a stationary "take-off" bar (not shown).

In one embodiment, the compaction step occurs in an indexed manner, where one set of tablets are compacted simultaneously, before rotating to another indexing station. In one embodiment, the compaction step occurs at a single indexing station and the application of energy occurs at a separate indexing station. In another embodiment, a third indexing station is present wherein the ejection of the tablet or multiple tablets occurs, wherein the lower forming tool is raised up through and up to the surface of the die platen. In another embodiment the compaction step is performed through the addition of air pressure or hydraulic cylinder to the top of the upper forming tooles. In one embodiment multiple tablets are ejected simultaneously and separated from the surface of the indexing station and removed via a take-off bar.

In another embodiment, the tablet shape may be prepared by the compaction methods and apparatus described in United States Patent Application Publication No. 20040156902. Specifically, the tablet shape may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder blend recovery system to recover excess powder blend from the filters and return the powder blend to the dies. In one embodiment the energy source (e.g., RF energy source) is projected through the die table of a rotary press into the appropriate heat source (e.g., thermal surface or electrode) within the punch or the die. In one embodiment the die table is constructed of non-conductive material.

In another embodiment, a portion of the powder blend may be prepared by a wet-granulation method, in which the excipients and a solution or dispersion of a wet binder (e.g., an aqueous cooked starch paste or solution of polyvinyl pyrrolidone) are mixed and granulated. Suitable apparatus for wet granulation include low shear mixers (e.g., planetary mixers), high shear mixers, and fluid beds (including rotary fluid beds). The resulting granulated material may then be dried, and optionally dry-blended with further ingredients (e.g., excipients such as, for example, the thermally-sensitive material described in the invention herein, lubricants, colorants, and the like). The final powder blend is then suitable for compaction by the methods described herein. Methods for direct compaction and wet granulation processes are known in the art.

In one embodiment, the tablet shape is prepared by the compaction methods and apparatus described in issued U.S. Pat. No. 6,767,200. Specifically, the tablet shape is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet shape may have one of a variety of different shapes. For example, the tablet shape may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet shape has one or more major faces. For example, the tablet shape surface typically has opposing upper and lower faces formed by contact with the upper and lower forming tool faces in the compaction machine. In such embodiments, the tablet shape surface typically further includes a "belly-band" located between the upper and lower faces, and formed by contact with the die walls in the compaction machine. A tablet shape/tablet may also be a multilayer.

In one embodiment, the method of producing the tablet shape is substantially free of the use of solvents. In this embodiment, the powder blend is substantially free of solvents, and the manufacturing process (e.g., filling process into the die) is also substantially free of solvents. Solvents may include, but are not limited to, water, organic solvents such as but not limited to alcohols, chlorinated solvents, hexanes, or acetone; or gaseous solvents such as but not limited to nitrogen, carbon dioxide or supercritical fluids.

In one embodiment a vibratory step is utilized (e.g., added after filling of the powder blend but prior to the heating or fusing step, in order to remove air from the powder blend). In one embodiment a vibration with the frequency from about 1 Hz to about 50 KHz is added with amplitude from 1 micron to 5 mm peak-to-peak to allow for the flowable powder blend to settle into the forming cavity of a the die ("die cavity").

In one embodiment, a lubricant is added to die cavity prior to the addition of the flowable powder blend. This lubricant may be a liquid or solid. Suitable lubricants include but are not limited to solid lubricants such as magnesium stearate, starch, calcium stearate, aluminum stearate and stearic acid; or liquid lubricants such as but not limited to simethicone, lecithin, vegetable oil, olive oil, or mineral oil. In certain embodiments, the lubricant is added at a percentage by weight of the tablet of less than 5 percent, e.g. less than 2 percent, e.g. less than 0.5 percent. In certain embodiments, the presence of a hydrophobic lubricant can disadvantageously compromise the disintegration properties of an orally disintegrating tablet. In one embodiment the tablet is substantially free of a hydrophobic lubricant. Hydrophobic lubricants include magnesium stearate, calcium stearate and aluminum stearate.

Heating of Tablet Shape to Form Tablet

Various forms of energy may be used in the process to heat the thermally-sensitive material. Suitable sources of energy include, but are not limited to, conduction, convection, radio frequency, microwave, UV light, infrared, induction, laser light, and ultrasonic sound.

In one embodiment, the tablet shape is in contact with the heat source. In one embodiment, the tablet shape is in physical contact with a thermal heat source. As depicted in FIG. 2, the heat source 100 may either heat the tablet shape along the horizontal axis, as shown with tablet shape 110 (having first region 115 and second region 105) or the vertical axis, as shown with tablet shape 110' (having first region 115' and second region 105').

Figure 3:
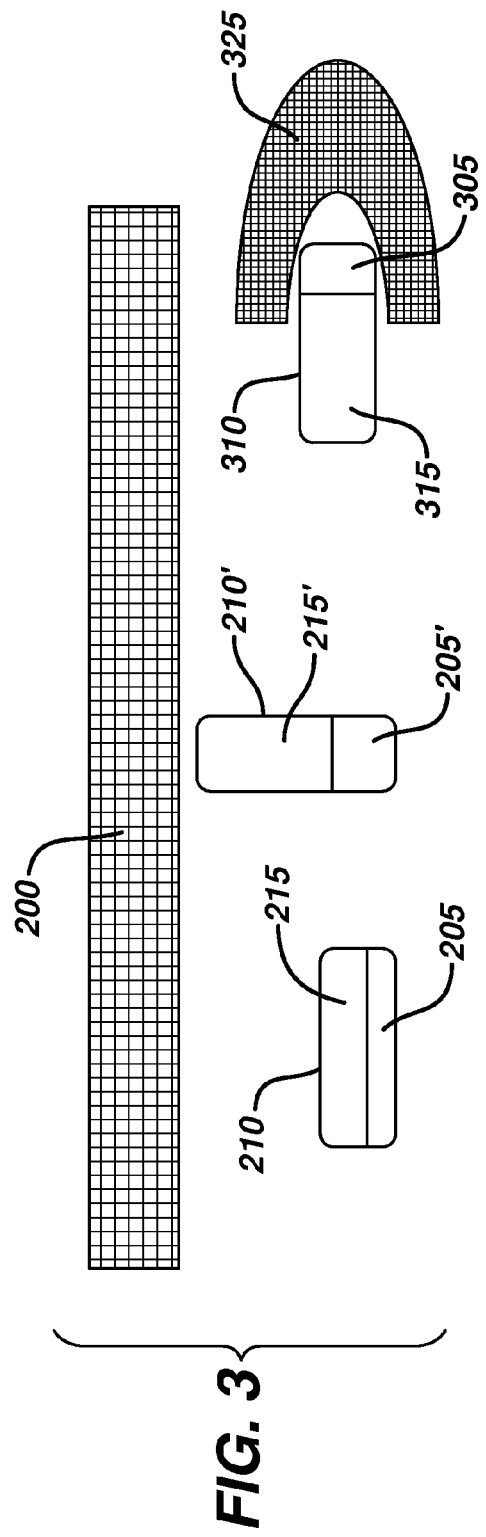
FIG. 3 is a side view of tablet shape 210/210'/310 being heated by energy source 200.

In one embodiment, the tablet shape is not in physical contact with the heat source. In one embodiment, the tablet shape is heated with an infrared heat source. As depicted in FIG. 3, the infrared heat source 200 may either heat the tablet shape along the horizontal axis, as shown with tablet shape 210 (having first region 215 and second region 205) or the vertical axis, as shown with tablet shape 210' (having first region 215' and second region 205'). In one embodiment, a portion of the tablet is shielded from the infrared energy (e.g., to maintain an immediate release region). Such an embodiment is depicted in FIG. 3 with a portion of tablet shape 310 being shielded by tablet shield 325. By having tablet shield 325 only covering a portion of tablet shape 310, the uncovered portion is exposed to infrared heat source 200, resulting in first region 310, while the covered portion is not so exposed to the heat source 200, resulting in second region 305.

In one embodiment, radiofrequency energy is used to heat the tablet shape. Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). The RF-energy is used to heat the binder (e.g., either directly when the meltable binder is a RF-meltable binder or indirectly when the meltable binder is not a RF meltable binder but is heated by a RF-heatable ingredient within the powder blend). The degree of compaction, the type and amount of meltable binder, and the amount of RF energy used can determine the hardness and/or type of lozenge.

RF energy generators are well known in the art. Examples of suitable RF generators include, but are not limited to, COSMOS Model C10X16G4 (Cosmos Electronic Machine Corporation, Farmingdale, N.Y.).

In one embodiment, the die and the forming tool (e.g., compaction punch) are serving as the electrodes (e.g., one can be the ground electrode) through which RF energy is delivered to the tablet shape. In one embodiment, there is direct contact between at least one electrode and the tablet shape. In another embodiment, there is no contact between any of the electrodes and the tablet shape. In one embodiment, the punches are in direct contact with the surface of the tablet shape when the energy is added. In another embodiment, the punches are not in contact (e.g., from about 1 mm to about 1 cm from the surface of the tablet shape) during the addition of the energy.

In one embodiment, the energy is delivered once the tablet shape is formed. In one embodiment, the energy is delivered continuously starting when the compaction begins. In one embodiment, the energy is delivered after the tablet shape has been removed from the die platen.

The forming tool and/or the forming cavity (e.g., forming cavity of the die platen) can optionally have electrically insulated side walls and/or can be fully electrically insulated. When RF energy is used, the RF energy can be delivered through insulated electrodes or through electrodes which are not in direct contact with the tablet shape or separated from the tablet shape by an air gap. In one embodiment, the die platen is non-conductive such that it cannot conduct RF energy, in that the energy is directly applied to the powder blend or pre-compacted form. In this embodiment, only the punches are conductive. In one embodiment, the die platen is constructed of plastic, polyethylene, high density polyethylene, polyvinylchloride, polypropylene, high density polypropylene, or Teflon®. In one embodiment, the forming tools (e.g., punches) are non-conductive and portions of the die platen act as two electrodes in order to direct and deliver the RF energy to the powder blend or pre-compacted form.

In one embodiment, to help reduce sticking, the tablet is cooled within the die cavity to cool and/or solidify the tablet shape to form a tablet. The cooling can be passive cooling (e.g., at room temperature) or active cooling (e.g., coolant recirculation cooling). When coolant recirculation cooling is used, the coolant can optionally circulate through channels inside the forming tools and/or die platen. In one embodiment, the process uses a die platen having multiple forming cavities and upper and lower forming tool platens having multiple upper and lower forming tools for simultaneous forming of a plurality of tablets wherein the platens are actively cooled.

In one embodiment, RF energy is combined with a second source of heat including but not limited to convection, conduction, infrared, induction, or convection heating. In one embodiment the powder blend provides resistance between two non-RF electrodes, and heat is generated as a result of resistance upon the addition of electricity.

In one embodiment, the powder blend is sealed within a chamber during the step with which the energy is applied, so that the water is contained and can be distributed throughout the powder blend. In one version of this embodiment, the sealed chamber consists of a forming cavity, and at least one heat source (e.g., RF applying electrode). In one embodiment, upon opening of the sealed chamber, the fused tablet is further dried in order to allow for the water to escape. This drying step may be achieved using the energy source or another source of heat.

In certain embodiments only certain portions of the surface area is treated with heat in order to modify the release rate of those portions. In one embodiment, up to 75% such as up to 50%, such as up to 25%, such as up to 10% of the area of the tablet is treated. In one embodiment, wherein the tablet has at least two faces, one face of the tablet is treated. In one embodiment, wherein the tablet has at least three faces (i.e. a top, middle and bottom), at least two of the faces are treated. In one version of this embodiment, the middle face comprises the belly-band of the tablet. In one embodiment, the tablet is a single layer tablet, comprising at least two faces and one face is treated.

Tablets Coatings

In one embodiment, the tablet includes an additional outer coating (e.g., a translucent coating such as a clear coating). Suitable materials for translucent coatings include, but are not limited to, hypromellose, hydroxypropylcellulose, starch, polyvinyl alcohol, polyethylene glycol, polyvinylalcohol and polyethylene glycol mixtures and copolymers, and mixtures thereof. Tablets of the present invention may include a coating from about 0.05 to about 10 percent, or about 0.1 to about 3 percent by weight of the total tablet.

Hardness

Because of the varying amount of heating through the tablet, and consequently the extent to which the thermally-sensitive material is melted or softened, the hardness of the tablet may differ at different portions of the tablet. In one embodiment, a portion of the first region has a hardness that is at least 10 percent greater than the hardness than a portion of the second region, such as at least 25 percent greater, such as at least 50 percent greater.

Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., Pharmaceutical Dosage Forms—Tablets, Volume 2, 2.sup.nd ed., Marcel Dekker Inc., 1990, pp. 213-217, 327-329.

A more preferred test for hardness of the tablet of the present invention relies upon a Texture Analyzer TA-XT2i that is fitted with a 7 millimeter diameter flat faced probe and setup to measure and report compression force in grams. The probe moves at 0.05 millimeters per second to a depth of penetration of 2 millimeters. The maximum compression force is recorded. In one embodiment, the measured forces recorded for tablets made in accordance with the present invention are less than 10,000 grams (e.g., less than about 1000 grams, such as less than about 700 grams. In one embodiment, the measured forces recorded for tablets made in accordance with the present invention ranges from about 100 grams to about 6000 grams, such as from about 100 grams to about 1000 grams, such as from about 75 grams to about 700 grams) with a deviation of ±50 grams. In another embodiment the measured forces recorded for tablets is less than 700 grams.

To determine the hardness of a particular region of the tablet, the region may first need to be isolated from the tablet.

Use of Tablet

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention is not confined to the specific limitations set forth in these examples.

Example 1

Preparation of Tablet Shapes Containing Acetaminophen (APAP) Active Agent

Tablet shapes were prepared with the ingredients set forth below in Table 1 as follows. One fifth of the starch and the acetaminophen, magnesium stearate, sodium starch glycolate were added to a Glatt GPCG 5/9 fluid bed granulator (commercially available from Glatt GMBH in Binzen, Germany) equipped with a top spray insert to produce a 2 kg batch of granulation. The remainder of the starch was added to warm water (60° C.) and mixed using a laboratory mixer until a slurry was formed. The starch slurry was sprayed onto the acetaminophen mixture at 20 g/minute and dried to less than 2 percent moisture to form the acetaminophen granulation. The carnauba wax was then added to a portion of the acetaminophen granulation to produce a 100 g blend which was blended end-over-end for 3 minutes in a plastic bag. A 645 mg tablet shape containing 500 mg of acetaminophen was then prepared by compressing the tablet utilizing simulated capsule like tooling ("caplet" tooling) utilizing a single station tablet press (commercially available from the Carver, Inc. company in Wabash, Ind.) and compressed at 3 tons.

TABLE 1

| Tablet shape Formulation | | | |
|---|---|---|---|
| Material | G/Batch | mg/tab | Weight % |
| Acetaminophen Granulation[1] | 93.41 | 602.7 | 93.41 |
| Carnauba Wax NF[2] | 6.59 | 42.5 | 6.59 |
| TOTAL | 100.0 | 645.2 | 100.0 |

[1]Acetaminophen granulation (APAP granulation) contains 83.0% Acetaminophen, 13.2% Powdered Starch, 3.3% sodium starch glycolate, and 0.53% magnesium stearate.
[2]Commercially available from Strahl and Batch, incorporated located in Villawood, Australia Example 2

Preparation and Evaluation of Various Ratios of Acetaminophen to Carnauba Wax

Tablet shapes were prepared as in Example 1 having various ratios of acetaminophen to carnauba wax as set forth in Table 2A. The tablet shapes were heated using an infrared sourced heat lamp with 250 watts of power and 120 volts. The tablet shapes were treated with different parameters as summarized in Table 2A. Specifically, the tablet shapes were either not heated, heated on one side, or heated on both sides, and if heated, they were positioned vertically or horizontally in relation to the lamp at a distance of 1, 2, or 5 mm and heated for 15, 30, 60, or 100 seconds on each heated side.

TABLE 2A

| Tablets with Varying Amounts of Acetaminophen to Carnuba Wax | | | | | |
|---|---|---|---|---|---|
| | Sample | | | | |
| | 2A | 2B | 2C | 2D | 2E |
| Carnauba Wax | 6.6% | 6.6% | 6.6% | 14.6% | 14.6% |
| APAP Granulation | 93.4% | 93.4% | 93.4% | 85.4% | 85.4% |
| Heat Treatment | non-treated | 30 sec | 50 sec | non-treated | 30 sec |
| Sides | N/A | One | Both | N/A | One |
| Distance | N/A | 5 mm | 2 mm | N/A | 2 mm |
| Position | Horizontal | Horizontal | Horizontal | N/A | Horizontal |

| | 2F | 2G | 2H | 2I |
|---|---|---|---|---|
| Carnauba Wax NF | 14.6% | 14.6% | 14.6% | 26.5% |
| APAP | 85.4% | 85.4% | 85.4% | 73.5% |
| Heat Treatment | 15 sec | 60 sec | 100 sec | 100 sec |
| Sides | One | One | One | One |
| Distance | 2 mm | 2 mm | 1 mm | 1 mm |
| Position | Horizontal | Horizontal | Vertical | Vertical |

The treated tablets from the previous examples were analyzed for dissolution utilizing USP Dissolution apparatus no. 2 at a paddle speed of 50 RPM. They were analyzed utilizing HPLC which sampled from zero up to four hours. The dissolution results are displayed in Table 2B and Table 2C.

TABLE 2B

| Dissolution Results (0-80 minutes) | | | | | | | | |
|---|---|---|---|---|---|---|---|---|
| | Time (Minutes) & Percent Released | | | | | | | |
| Sample | 0 | 10 | 20 | 30 | 40 | 50 | 60 | 80 |
| Sample 2A | 0 | 100.8 | 100.7 | 100.7 | 100.8 | 100.8 | 100.7 | 100.8 |
| Sample 2B | 0 | 40.2 | 61.1 | 80.1 | 88.4 | 94.4 | 99.5 | 99.8 |
| Sample 2C | 0 | 43.5 | 69.1 | 83.5 | 88.7 | 92.8 | 98.2 | 99.6 |

TABLE 2B-continued

Dissolution Results (0-80 minutes)

| | Time (Minutes) & Percent Released | | | | | | | |
|---|---|---|---|---|---|---|---|---|
| Sample | 0 | 10 | 20 | 30 | 40 | 50 | 60 | 80 |
| Sample 2D | 0 | 87.8 | 97.6 | 98.4 | 98.6 | 98.7 | 98.7 | 98.6 |
| Sample 2E | 0 | 6.9 | 19.0 | 33.3 | 48.0 | 60.5 | 71.4 | 88.4 |
| Sample 2F | 0 | 89.3 | 99.3 | 99.5 | 99.7 | 99.8 | 99.7 | 100.7 |
| Sample 2G | 0 | 8.1 | 19.5 | 29.2 | 40.4 | 50.8 | 58.9 | 72.1 |
| Sample 2H | 0 | 50.3 | 60.1 | 67.5 | 70.1 | 72.8 | 78.5 | 87.2 |
| Sample 2I | 0 | 56.9 | 64.0 | 68.9 | 71.4 | 73.7 | 77.3 | 83.6 |
| Reference* | 0 | 99.6 | 99.9 | 99.9 | 99.9 | 99.9 | 99.9 | 100.0 |

TABLE 2C

Dissolution Results (90-160 minutes)

| | Time (Minutes) & Percent Released | | | |
|---|---|---|---|---|
| Sample | 90 | 100 | 120 | 160 |
| Sample 2A | 100.8 | 100.8 | 100.7 | 100.6 |
| Sample 2B | 99.8 | 99.8 | 99.6 | 99.6 |
| Sample 2C | 99.7 | 99.7 | 99.7 | 99.6 |
| Sample 2D | 98.7 | 98.7 | 98.7 | 98.8 |
| Sample 2E | 94.8 | 98.1 | 100.0 | 100.2 |
| Sample 2F | 100.5 | 100.5 | 100.5 | 100.1 |
| Sample 2G | 77.9 | 82.8 | 90.8 | 98.9 |
| Sample 2H | 91.5 | 94.5 | 97.9 | 99.3 |
| Sample 2I | 86.1 | 88.7 | 92.1 | 96.3 |
| Reference* | 100.1 | 100.2 | 100.1 | 99.9 |

*Reference: Tylenol Rapid Release Gel, commercially available from McNeil Consumer Healthcare in Fort Washington, PA The dissolution results demonstrate that the tablet shapes in which the carnauba wax was added and not subsequently heated (e.g., Samples 2A and 2F and the Reference) did not have sustained release profiles, while those that were heated did have sustained release profiles. The dissolution profiles from 2E and 2G demonstrate that the higher level of wax in the formulation and the longer duration of treatment (30 sec and 60 sec) on the horizontal axis created the highest level of sustained release property (e.g., slowest release of acetaminophen). Further, these results demonstrate that by modifying the amount of energy applied to the tablets, the release profiles for the tablets could also be modified.

Example 3

Preparation of Acetaminophen Tablet Shapes for Hot Plate Treatment

Tablet shapes were prepared containing 500 mg acetaminophen utilizing granulation, commercially sold under the trade-name of COMPAP® from Mallicrodt, Inc. in Hazelwood, Mo. The granulation contains 97 percent acetaminophen and 3 percent polyvinylpyrrolidone (povidone). 100 g batches were blended end-over-end for approximately 3 minutes in a plastic bag with carnauba wax and sodium starch glycolate according to the ratios in Table 3A. The blends were compressed on a single station tablet press, at a pressure of 3 tons, utilizing caplet shaped tooling (0.750"×0.250"×0.075"). The tablet shapes were either not treated ("Sample 3A") or treated by placing on side of the tablet shape on the surface of a hot plate at 140 to 160° C. for 100 seconds ("Sample 3B-3F").

TABLE 3A

Acetaminophen Tablet Compositions for Hot Plate Treatment

| | Sample | | | | | |
|---|---|---|---|---|---|---|
| Material | 3A | 3B | 3C | 3D | 3E | 3F |
| Sodium Starch Glycolate[1] | 2.9% | 2.9% | 2.9% | 2.9% | 2.9% | 3.0% |
| Carnauba Wax NF[2] | 6.9% | 6.9% | 6.9% | 6.9% | 15.2% | 26.2% |
| APAP granulation | 87.4% | 87.4% | 87.4% | 87.4% | 79.5% | 68.7% |
| Heat Treatment | None | 100 sec | 150 sec | 100 sec | 100 sec | 100 sec |
| Sides | N/A | One | One | Both | One | One |

[1]Commercially available from Roquette Corporation in Lestrem, France under the trade-name of Glycolys ®
[2]Commercially available from Strahl and Batch, incorporated located in Villawood, Australia The treated tablets from the previous examples were analyzed for dissolution utilizing USP Dissolution apparatus no. 2 at a paddle speed of 50 RPM. They were analyzed utilizing HPLC which sampled from zero up to four hours. The dissolution results are displayed in Table 3B.

TABLE 3B

Dissolution Results

| | Time (Minutes) & Percent Released | | | | | | | | |
|---|---|---|---|---|---|---|---|---|---|
| Sample | 0 | 5 | 10 | 15 | 30 | 60 | 120 | 180 | 240 |
| Sample 3A | 0 | 89.5 | 99.3 | 99.8 | 99.5 | 100.8 | 100.6 | 100.3 | 100.0 |
| Sample 3B | 0 | 34.0 | 41.6 | 44.4 | 53.5 | 69.7 | 93.6 | 99.8 | 100.0 |
| Sample 3C | 0 | 16.2 | 21.3 | 24.4 | 34.4 | 53.5 | 82.9 | 98.0 | 100.0 |
| Sample 3D | 0 | 5.7 | 9.8 | 13.6 | 26.3 | 54.6 | 88.0 | 100.2 | 100.0 |
| Sample 3E | 0 | 44.1 | 57.7 | 62.9 | 70.5 | 81.9 | 94.8 | 100.2 | 100.0 |

The dissolution results demonstrate that the tablet shape in which the sodium starch glycolate and carnauba wax was added and not subsequently heated (e.g., Samples 3A) did not have sustained release profiles, while those that were heated did have sustained release profiles. Of note, Sample 3D, in which both sides were heated for 100 seconds, displayed a slow release profile (with less than 10% being released within the first 10 minutes). The results demonstrate that the sample treated for the longest period of time (Sample 3C) and the sample treated on both sides (Sample 3D) had the longest sustained release property with the slowest release profiles.

Example 4

Preparation of Phenylephrine Tablet Shapes for Hot Plate Treatment

Tablet shapes were prepared containing 30.0 mg phenylephrine. 100 g batches were blended end-over-end for approximately 3 minutes in a plastic bag with carnauba wax, sodium starch glycolate, and silicified microcrystalline cellulose according to the ratios in Table 4A. The blends were compressed on a single station Carver tablet press, at a pressure of 3 tons, utilizing caplet shaped tooling (0.750"×0.250"×0.075"). The tablets were heated on by placing the tablet horizontally on the surface of a hot plate at 130 to 160° C. for either 60 seconds or 100 seconds on one side.

TABLE 4A

Phenylephrine tablet shapes for Hot Plate Treatment

| Material | Sample 4A | Sample 4B |
|---|---|---|
| Phenylephrine HCl | 4.7% | 4.7% |
| Carnauba Wax | 23.1% | 23.1% |
| Sodium Starch Glycolate | 3.0% | 3.0% |
| Silicified Microcrystalline Cellulose[1] | 69.2% | 69.2% |
| Heat Treatment | 60 sec | 100 sec |

[1] Commercially available under the trade-name of Prosolv ® SMC50 from JRS Pharma in Patterson, New York
2. Commercially available under the trade-name of Fujicalin ® from FUJI Chemical in Yokohoonji, Kamiichi-machi Nakaniikawa-gun, Toyama-Pref., Japan The treated tablets from the previous examples were analyzed for dissolution utilizing USP Dissolution apparatus no. 2 at a paddle speed of 50 RPM. They were analyzed utilizing HPLC which sampled from zero up to four hours. The dissolution results are displayed in Table 4B.

TABLE 4B

Dissolution Results

| Sample | \multicolumn{9}{c}{Time (Minutes) & Percent Released} |
|---|---|---|---|---|---|---|---|---|

| Sample | 0 | 5 | 10 | 15 | 30 | 60 | 120 | 180 | 240 |
|---|---|---|---|---|---|---|---|---|---|
| Sample 4A | 0 | 19.0 | 39.2 | 51.9 | 72.2 | 96.2 | 98.7 | 98.7 | 100.0 |
| Sample 4B | 0 | 38.3 | 54.2 | 61.7 | 79.4 | 96.3 | 99.1 | 99.1 | 100.0 |

The dissolution results demonstrate that the tablets had a fast initial release followed by a sustained release profile

Example 5

Preparation of Guaifenesin Tablet Shapes for Infrared Lamp Treatment

Tablet shapes were prepared containing 500.0 mg guaifenesin. 100 g batches were blended end-over-end for approximately 3 minutes in a plastic bag with carnauba wax and sodium starch glycolate according to the ratios in Table 5A. The blends were compressed on a single station tablet press, at a pressure of 3 tons, utilizing caplet shaped tooling (0.750"×0.250"×0.075"). The tablets were either not heated or heated by first shielding half of the length of the tablet within a metal tube and then placing the half-shielded tablet horizontally under a 250 Watt infrared lamp at a distance of 1 inch for 2 minutes such that the unshielded half of the tablet was exposed to the IR energy.

TABLE 5A

Guaifenesin tablet shapes for Infrared Lamp Treatment

| Material | Sample 5A | Sample 5B | Sample 5C |
|---|---|---|---|
| Guaifenesin | 89.0% | 89.0% | 89.0% |
| Carnauba Wax | 10.8% | 10.8% | 10.8% |
| Sodium Starch Glycolate | 0.2% | 0.2% | 0.2% |
| Heat Treatment | None | 2 min | 2 min |

The tablets were analyzed for dissolution utilizing USP Dissolution apparatus no. 2 at a paddle speed of 50 RPM. They were analyzed utilizing HPLC which sampled from zero up to four hours. The dissolution results are displayed in Table 5B.

TABLE 5B

Dissolution Results

| Sample | 0 | 5 | 10 | 15 | 30 | 60 | 120 | 180 | 240 |
|---|---|---|---|---|---|---|---|---|---|
| Sample 5A | 0 | 96.2 | 99.1 | 99.1 | 100.0 | 100.0 | 100.0 | 100.0 | 100.0 |
| Sample 5B | 0 | 41.4 | 47.4 | 51.7 | 66.4 | 81.0 | 99.1 | 100.0 | 100.0 |
| Sample 5C | 0 | 52.6 | 62.2 | 65.9 | 74.8 | 87.4 | 98.5 | 99.3 | 100.0 |

The dissolution results demonstrate that the tablet shape in which the sodium starch glycolate and carnauba wax was added and not subsequently heated (e.g., Samples 5A) did not have sustained release profiles, while those that were heated did have sustained release profiles. Of note, the profile demonstrates that tablets containing guaifenesin with an immediate release profile can be made to further have a sustained release profile upon the addition of heat.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

The invention claimed is:

1. A process for making a tablet comprising a pharmaceutically active agent wherein said tablet comprises both an immediate release region and a modified release region, said method comprising the steps of:
    (a) forming a tablet shape comprising a powder blend comprising a pharmaceutically active agent and a thermally-sensitive material; and
    (b) applying energy in different amounts to different regions of the surface of the tablet shape to form said tablet in a manner such that:
        (i) a first region of said tablet shape is exposed to said energy for a sufficient period of time to modify said thermally-sensitive material within said first region to form said modified release region of said tablet; and
        (ii) a second region of said tablet shape is not so exposed to said energy such that said second region forms said immediate release region of said tablet.

2. The process of claim 1, wherein said thermally-sensitive material is a meltable material having a melting point of from about 20° C. to about 140° C. and said first region is exposed to said energy for a sufficient period of time to melt said meltable material.

3. The process of claim 1, wherein said tablet shape is formed by compressing said powder blend.

4. The process of claim 3, wherein said powder blend is compressed in a die platen and said energy is applied to said tablet shape within said die platen.

5. The process of claim 1, wherein said first region comprises at least 20%, by weight, of said tablet, and said second region comprises at least 20%, by weight, of said tablet.

6. The process of claim 1, wherein from about 1 to 50 percent is released in the 60 minutes following oral ingestion and about 50 to 99 percent is released from about 60 minutes to about 24 hours after oral ingestion.

7. The process of claim 1, wherein said energy is selected from group consisting of conduction, convection, radio frequency, microwave, UV light, infrared, induction, laser light, and ultrasonic sound.

8. The process of claim 1, wherein said energy is conduction, convection or infrared energy.

9. The process of claim 1, wherein said thermally-sensitive material is selected from the group consisting of waxes, fats, fatty acid esters, polymers and phospholipids, or a mixture thereof 10. The process of claim 1, wherein said thermally-sensitive material is selected from the group consisting of carnauba wax, spermaceti wax, beeswax, candelilla wax, shellac wax, microcrystalline wax, and paraffin wax, or a mixture thereof.

11. The process of claim 1, wherein said powder blend comprises from about 5 to about 50 percent, by weight, of said thermally-sensitive material.

12. The process of claim 4, wherein said process comprises the steps of:
 (i) introducing said powder blend into a forming cavity within said die platen;
 (ii) compacting said powder blend by introducing at least one forming tool into said die platen with sufficient force such that a tablet shape is formed;
 (iii) applying said energy to said tablet shape within said forming cavity to form said tablet; and
 (iv) removing said tablet from said forming cavity.

13. The process of claim 2, wherein said at least one said punch applies said energy to said tablet shape.

14. The process of claim 1, wherein the powder blend within the first region is the same as the powder blend of the second region prior to application of said energy.

15. The process of claim 1, wherein said process comprises the steps of:
 (i) introducing said powder blend into a forming cavity within said die platen;
 (ii) compacting said powder blend by introducing at least one forming tool into said die platen with sufficient force such that a tablet shape is formed;
 (iii) removing said tablet shape from said forming cavity; and
 (iv) applying said energy to said tablet shape to form said tablet.

* * * * *